(12) United States Patent
Ye

(10) Patent No.: US 9,289,540 B2
(45) Date of Patent: Mar. 22, 2016

(54) SURFACE MODIFICATION FOR COATING

(75) Inventor: Qingshan Ye, Plymouth, MN (US)

(73) Assignee: Greatbatch Ltd., Clarence, NY (US)

(*) Notice: Subject to any disclaimer, the term of this patent is extended or adjusted under 35 U.S.C. 154(b) by 478 days.

(21) Appl. No.: 12/776,095

(22) Filed: May 7, 2010

(65) Prior Publication Data

US 2010/0286766 A1 Nov. 11, 2010

Related U.S. Application Data

(60) Provisional application No. 61/176,582, filed on May 8, 2009.

(51) Int. Cl.
| | |
|---|---|
| A61L 33/00 | (2006.01) |
| B32B 27/28 | (2006.01) |
| B32B 27/36 | (2006.01) |
| B32B 27/34 | (2006.01) |
| B32B 27/40 | (2006.01) |

(52) U.S. Cl.
CPC .......... *A61L 33/0017* (2013.01); *B32B 27/283* (2013.01); *B32B 27/285* (2013.01); *B32B 27/34* (2013.01); *B32B 27/365* (2013.01); *B32B 27/40* (2013.01); *B32B 2535/00* (2013.01); *Y10T 428/263* (2015.01); *Y10T 428/265* (2015.01); *Y10T 428/31507* (2015.04); *Y10T 428/31551* (2015.04); *Y10T 428/31678* (2015.04); *Y10T 428/31725* (2015.04)

(58) Field of Classification Search
CPC A61L 33/0017; B32B 27/283; B32B 27/285; B32B 27/34; B32B 27/365; B32B 27/40; B32B 2535/00
See application file for complete search history.

(56) References Cited

U.S. PATENT DOCUMENTS

| | | | |
|---|---|---|---|
| 4,528,343 A | 7/1985 | Kira | |
| 4,540,538 A | 9/1985 | Corwin | |
| RE32,325 E | 1/1987 | Smith | |
| 4,634,743 A | 1/1987 | Prier | |
| 5,229,431 A | 7/1993 | Pinchuk | |
| 5,530,083 A | 6/1996 | Phelps | |
| 5,741,852 A | 4/1998 | Marchant | |
| 5,863,627 A | 1/1999 | Szycher | |
| 5,873,904 A | 2/1999 | Ragheb | |
| 5,993,890 A | 11/1999 | Marchant | |
| 6,342,591 B1 | 1/2002 | Zamora | |
| 6,759,388 B1 | 7/2004 | Marchant et al. | |
| 6,841,255 B2 | 1/2005 | Deppisch | |
| 7,026,423 B2 | 4/2006 | Gunatillake | |
| 7,135,538 B2 | 11/2006 | Glasgow | |
| 7,202,325 B2 * | 4/2007 | Pacetti et al. | 528/272 |
| 7,276,474 B2 | 10/2007 | Marchant | |
| 7,468,210 B1 | 12/2008 | Zamora | |
| 2002/0115836 A1 | 8/2002 | Tsang | |
| 2002/0160098 A1 | 10/2002 | Zamora | |
| 2003/0018306 A1 | 1/2003 | Bucay-Couto et al. | |
| 2003/0031699 A1 | 2/2003 | Van Antwerp | |
| 2004/0039437 A1 | 2/2004 | Sparer | |
| 2004/0146715 A1 | 7/2004 | Guire et al. | |
| 2004/0151764 A1 | 8/2004 | Zamora | |
| 2004/0215336 A1 * | 10/2004 | Udipi et al. | 623/1.42 |
| 2005/0244459 A1 | 11/2005 | DeWitt | |
| 2005/0255317 A1 * | 11/2005 | Bavaro et al. | 428/375 |
| 2006/0199764 A1 | 9/2006 | Zamora | |
| 2008/0262614 A1 | 10/2008 | Marchant | |

FOREIGN PATENT DOCUMENTS

| | | | | |
|---|---|---|---|---|
| JP | 2003327986 A | * | 11/2003 | ........... C10M 133/16 |
| WO | 2006047289 | | 5/2006 | |

OTHER PUBLICATIONS

Machine translation of JP 2003327986 (2014).*
Vacheethasanee, Katanchalee, et al., "Surfactant polymers designed to suppress bacterial (*Staphyloccus epidermidis*) adhesion on biomaterials", S. Epidermis-Resistant Surfaces, 2000, p. 302-312, John Wiley & Sons, Inc.
Qiu, Yongxing, et al., "Novel Nonionic Oligosaccharide Surfactant Polymers Derived from Poly(vinylamine) with Pendant Dextran and Hexanoyl Groups" Macromolecules, Jan. 13, 1998, p. 165-171, vol. 13, No. 1, American Chemical Society.
European Search Report dated Mar. 29, 2012.
Arkles, Barry, "Hydrophobicity, Hydrophilicity and Silanes", Paint and Coatings Industry Magazine, Oct. 2006.

* cited by examiner

*Primary Examiner* — Callie Shosho
*Assistant Examiner* — John Freeman
(74) *Attorney, Agent, or Firm* — Steven W. Winn

(57) ABSTRACT

A modified medical device substrate surface designed to improve adhesion of biomimetic surfactants to the medical device surface, thus reducing the risk of thrombosis is described. The surface modification is accomplished through either an application of a tie layer of a hydrophobic material on the substrate surface intermediate the biomimetic coating or through incorporation of a hydrophobic dopant in the polymeric substrate prior to extrusion or molding. Either method creates a hydrophobically modified surface that enhances the biomimetic surfactant bonding strength.

15 Claims, 3 Drawing Sheets

SURFACE MODIFICATION FOR COATING

CROSS-REFERENCE TO RELATED APPLICATION

The present application claims priority from U.S. Provisional Application Ser. No. 61/176,582, filed May 8, 2009.

BACKGROUND OF THE INVENTION

1. Field of the Invention

The present invention is related generally to biocompatible coatings. More specifically, the present invention is related to the modification of medical device surfaces for the application of biocompatible coatings.

2. Background Art

Implantable medical devices including, pacemakers, defibrillators, neurostimulators, venous introducers, and catheters are devices that are well known to help improve health and sustain life. However despite the significant benefits that implantable medical devices provide, their use could lead to thrombosis, a serious medical problem that could result in death. Thrombosis is the formation of a blood clot within a blood vessel that obstructs blood flow leading to possible stroke, heart attack, organ failure and death.

Medical device related thrombosis initially occurs as a result of an interaction between blood and the surface of the medical device when they are in contact with each other. Once blood is in contact with the medical device, blood platelets and other blood constituents begin to coagulate and clot on the device surface. Blood clotting is known to occur on both metallic and polymeric materials, materials which are used to manufacture medical devices.

After the formation of the blood clots have occurred on the device surface, the clots could break off from the surface, travel through the blood stream, become lodged in a blood vessel and obstruct blood flow. Thrombosis is an especially major problem for permanently implanted devices that are in continuous blood contact.

A great deal of work has been done to develop coatings which reduce cell adhesion and activation. These coatings, referred to as biomimetic coatings, can inhibit the formation of blood clots and therefore reduce the possibility of thrombosis from occurring.

One such family of biomimetic coatings are surfactants described by Marchant et al. in U.S. Pat. Nos. 6,759,388 and 7,276,474 and U.S. patent application publications 20080247988 and 20080262614, which are herein incorporated by reference.

These coatings provide good blood clot inhibition. However, adhesion of these coatings to many medical device surfaces, particularly those device surfaces that are in constant contact with blood, could benefit from improved coating adhesion. In particular, adhesion to polymeric surfaces specifically made of silicone, polyurethane and polyether block amide (PEBA) materials are not ideal.

An objective of the present invention, therefore, is to provide a means of modifying the surface of the medical device to improve the adhesion of the biomimetic polymer coatings over a wider range of medical device surfaces.

SUMMARY OF THE INVENTION

The present invention relates to the modification of material substrates that are used in implantable medical devices to improve adhesion of biomimetic surfactant coatings. Biomimetic surfactants, which will be discussed in more detail, are designed to reduce protein, platelet and leukocyte adhesion, and as a result, reduce the likelihood of thrombosis.

The biomimetic surfactant coatings developed by Marchant et al. are known to reduce platelet adhesion and activation on the coating surface. Adhesion of the coating to the substrate surface is largely controlled through hydrophobic interactions between the surfactant and the substrate surface. Adhesive strength varies and depends on substrate chemistry. Adhesive strength is proportional to substrate surface hydrophobity. The higher the substrate surface hydrophobity, the stronger the adhesive bond between the substrate surface and surfactant coating.

Common medical device substrates are of silicone, polyurethane and polyether block amides. The latter material is manufactured under the "Pebax" trade name. These polymeric materials are often used in the construction of a wide range of medical devices that include catheters, intravenous introducers, pacemakers, defibrillators, neurostimulators, and their associated leads.

Therefore, it is desirable to modify the surface of these materials by increasing their hydrophobicity to further improve adhesion to the biomimetic surfactant.

The present invention does just that. It modifies the substrate surface and thus its hydrophobicity through two embodiments. The first embodiment modifies the substrate surface through the application of a "tie layer" with increased hydrophobicity. This "tie layer" is placed on the substrate surface and forms a composite bond between the substrate surface and the biomimetic coating. The "tie layer" serves as an intermediate layer that improves bonding of the biomimetic surfactant coating to that of the medical device surface. The second embodiment modifies the substrate surface through the incorporation of a dopant with increased hydrophobicity that is added during processing of the substrate material. The addition of the dopant results in a substrate surface with increased hydrophobicity.

The term "hydrophobic" is defined herein as repelling, tending not to combine with, or incapable of dissolving in water. The term "biomimetic" is defined herein as mimicking bodily cell interaction at the molecular level so as not to cause an adverse affect or reaction in the body. The term "non-thrombogenic" is defined herein as prohibiting the coagulation of blood from occurring in a blood vessel. The term "substrate" is defined herein as a base material which can be modified through the application of a surface coating or through the incorporation of dopant materials during processing of the base material. As referred to in this present invention, a substrate surface refers to the surface of a medical device.

Once the polymeric surface has been sufficiently modified, a biomimetic surfactant polymer such as poly(N-vinyldextran aldonamide-co-N-vinylhexanamide) or its derivatives is applied onto the hydrophobically modified substrate surface.

The biomimetic surfactant comprises a polymeric backbone of repeating monomeric units having functional groups for coupling with side chains. The surfactant comprises two main functional groups, a hydrophobic side chain functional group and a hydrophilic side chain functional group. The hydrophobic side chain affects the bonding adhesion of the surfactant to the substrate surface. The hydrophilic side chain functional group controls the biomimetic properties of the surfactant and creates an effective non-thrombogenic surface that retards blood clotting.

A polymer tie layer comprising parylene, silicone polycarbonate co-polymers, polyurethane polycarbonate co-polymers, or an unsaturated long chain carboxylic acid amide, such as erucamide, is first applied to the substrate surface of the medical device. After the hydrophobic polymer layer is applied, a biomimetic surfactant is then applied over the initial hydrophobic polymer layer. The initial hydrophobic polymer layer acts as an intermediate or tie layer that bonds the biomimetic coating to the material of the device surface.

Therefore, with the use of an intermediary tie layer, the modified medical device surface has a hydrophobicity that is sufficient to form a secure adhesive bond to the biomimetic surfactant.

The hydrophobicity of the substrate surface can also be increased with the addition of an unsaturated long chain carboxylic acid amide, such as erucamide, added as a dopant. Incorporating a small amount of an unsaturated long chain carboxylic acid amide into polymers, such as polyurethane, during formulation results in a polyurethane substrate having a surface with increased hydrophobicity. The polymer surface therefore has a hydrophobic surface that is adequate to form a secure adhesive bond to the biomimetic surfactant.

DETAILED DESCRIPTION OF THE PREFERRED EMBODIMENTS

Figure 1:
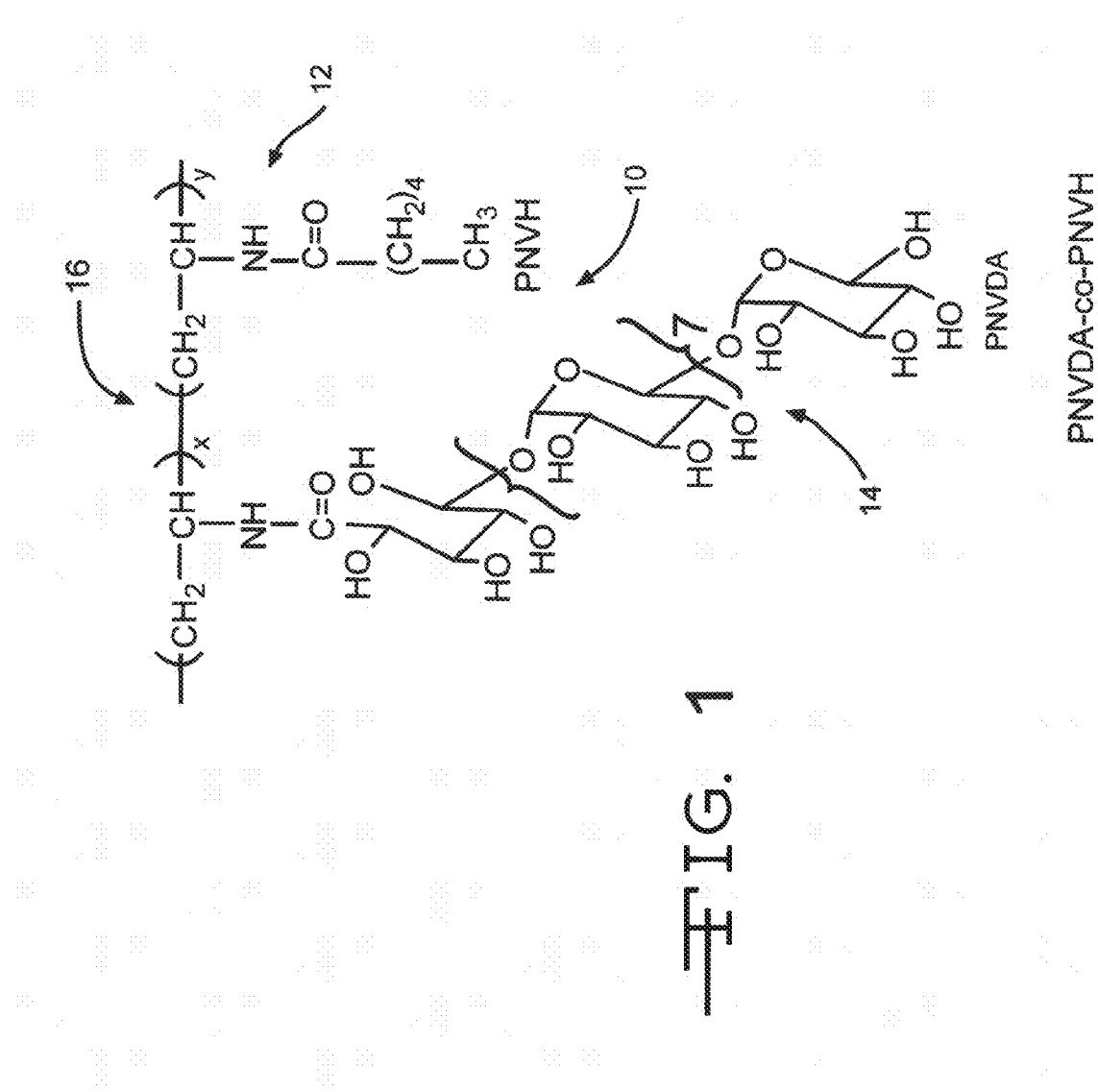
FIG. 1 is a depiction showing the chemical structure of the biomimetic surfactant used in the present invention.

In the present invention, the surface of a substrate is modified to improve the adhesion of a preferred biomimetic surfactant, poly(N-vinyldextran aldonamide-co-N-vinylhexanamide), to the surface of a medical device to reduce the occurrence of thrombosis. As shown in FIG. 1, the biomimetic surfactant comprises a chemical structure 10 that is composed of a combination of a hydrophobic molecular chain and a hydrophilic molecular chain. The hydrophobic molecular chain comprises a poly(N-vinyl hexanoyloxy) (PNVH) component 12 and the hydrophilic molecular chain comprises a poly(N-vinyl dextran aldonamide) (PNVDA) component 14. The molecular weight of the preferred surfactant ranges from about 1,000 to about 2,000,000 dalton.

The biomimetic surfactant is applied to the substrate surface through the application of a coating. Preferred polymeric substrate materials comprise silicone, polyurethane and a polyether block amide, known under the trade name "Pebax". It is contemplated that the surfaces of such medical devices as pacemakers, defibrillators, neurostimulators, introducers, leads, catheters and stents can be modified.

Alternate biomimetic surfactants comprising poly(N-vinyl dextran aldonamide-co-N-vinyl dodecanoamide) (PNVDA-co-PNVL), poly(N-vinyl hexyl amine-co-N-vinyl heparinamine) (PNVHA-co-PNVHep A), poly(N-vinyl hexyl amine-co-N-vinyl heparinamine-co-N-vinyl maltonoamide) (PNVHA-co-PN-VHepA-co-PNVM), and poly(N-vinyl-5-peptidyl-pentylamine-co-N-vinyl-dextranaldonamine-co-N-vinyl hexyl amine (PVAm(Pep:Dex:Hex)) can also be used.

As illustrated in FIG. 1, the preferred biomimetic surfactant has a comb-like structure that comprises a flexible polymeric backbone 16 that is linked to a combination of a plurality of hydrophobic side chains, poly(N-vinyl hexanoamide) (PNVH) 12 and a plurality of hydrophilic side chains, poly(N-vinyl dextran aldonamide) (PNVDA), 14.

The hydrophobic side chains 12 comprise alkyl groups that are linked to the polymeric backbone 16 via an ester linkage, an amine linkage or an amide linkage. Preferably, the hydrophobic chains 12 are attached to the polymeric backbone 16 by reacting an alkanoyl ($CH_3(-CH_2-)nCO—$) or an alkanal ($CH_3(CH_2-)nCHO$) with the homopolymer of the backbone.

In the present invention, the alkyl chain of the biomimetic surfactant molecule is hydrophobic and associates with the hydrophobic entity (tie layer or dopant) of the substrate surface, via hydrophobic interaction. The aqueous environment of the surfactant repels the surfactant hydrophobic alkyl chain toward the substrate hydrophobic entity. This hydrophobic-hydrophobic association creates a bond between the biomimetic coating and the substrate hydrophobic entity.

As previously mentioned, the hydrophilic side chain controls the biomimetic properties of the surfactant. To form a coating which blocks adhesion of non-specific plasma proteins on the surface of the substrate, the surfactant polymer preferably comprises a plurality of hydrophilic side chains formed from oligosaccharides with an average molecular weight of less than 7000 dalton. Such surfactant polymers may be ionic or non-ionic and are not limited to natural oligosaccharides, such as dextran. The hydrophilic side chains are linked to the polymeric backbone 16 through an ester linkage, a secondary amine linkage or preferably an amide linkage.

Alternatively, a charged oligosaccharide, preferably of a negatively charged oligosaccharide having an average molecular weight less than 10,000 dalton, and an oligopeptide containing about 3 to about 30 amino acid residues of the oligopeptide is preferred. The amino acid sequence of the oligopeptide interacts with protein receptors on the surface of the cells such as endothelial cells.

The substrate surface can be modified in either of two preferred methods. The first preferred method utilizes the application of a tie layer, a coating whereby a polymer layer with increased hydrophobicity is first applied to the substrate surface. The polymer tie layer is directly applied to the bare substrate surface and acts as an intermediate layer that facilitates bonding between the substrate i.e., the surface of the medical device, and the biomimetic surfactant coating.

In the second preferred method, a hydrophobic modifier is doped into the substrate material and incorporated into the substrate polymeric material during formulation of the substrate. This method results in a substrate material with increased surface hydrophobicity that is capable of forming a strong adhesive bond to the biomimetic surfactant. Unlike the coating method, the dopant modification embodiment does not require the use of a tie layer to secure the non-thrombogenic coating to the substrate surface.

Figure 2:
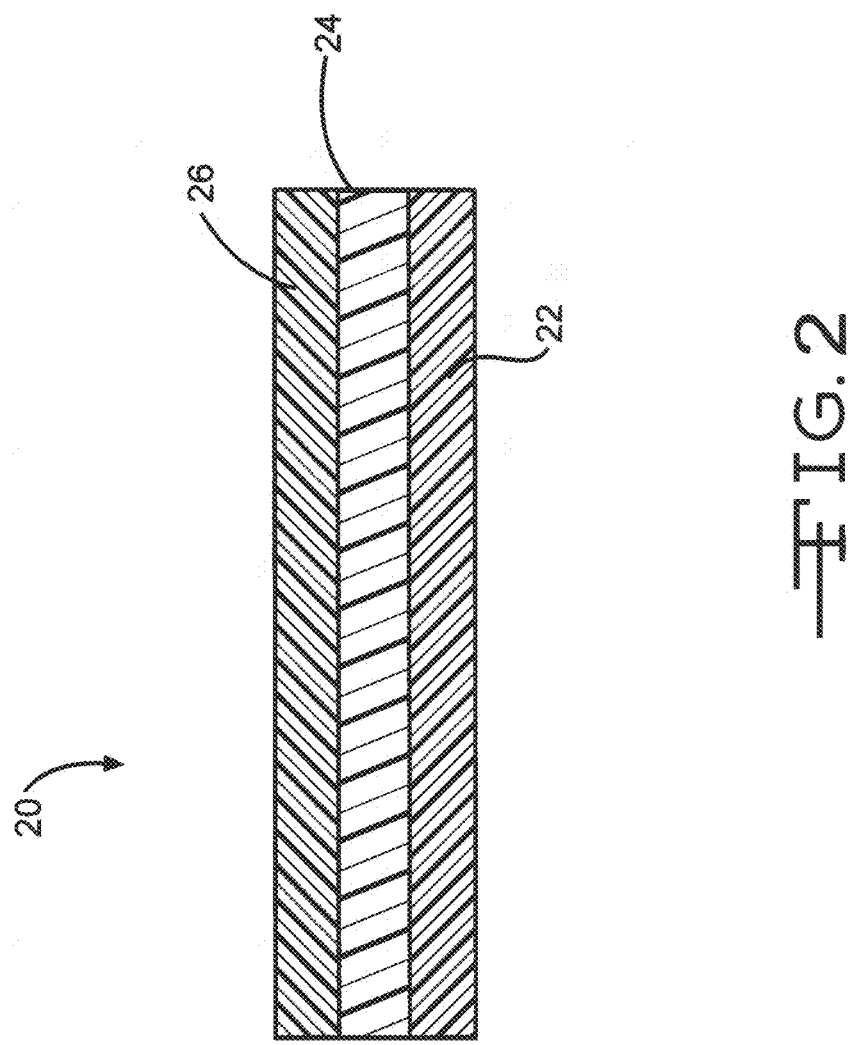
FIG. 2 is a cross-sectional view showing the tie layer sandwiched between the substrate surface and the biomimetic coating.

In the preferred tie layer method, thin layers of a hydrophobic polymeric material are first applied to a clean bare substrate surface. Preferred hydrophobic polymeric materials include parylene, silicone polycarbonate co-polymer, polyurethane polycarbonate co-polymer and an unsaturated long chain carboxylic acid amide, such as erucamide. The thin layer or layers of the hydrophobic tie layer material are sandwiched between the substrate material and the biomimetic coating material. FIG. 2 illustrates an example embodiment of a substrate surface which has been modified with the application of a tie layer. As the figure shows, a composite 20 is created in which the top surface of the substrate 22 bonds to the bottom surface of the hydrophobic tie layer 24 and the bottom surface of the biomimetic surfactant coating 26 bonds to the top surface of the tie layer 24.

In a first preferred embodiment, parylene is applied using vapor deposition. A layer of parylene of about 2.5 nanometers is directly applied to a clean bare substrate surface. Multiple layers ranging in thickness from about 1 to 3000 nanometers could also be applied.

In a second preferred tie layer coating embodiment, a layer of an unsaturated long chain carboxylic acid amide, such as erucamide, is applied to the substrate surface. First, a tie layer solution comprising erucamide and tetrahydrofuran (THF) solution is created by dissolving erucamide in THF. A preferred amount ranging from about 0.1 to 10 weight percent of erucamide is added to the tetrahydrofuran solvent.

A tie layer with a preferred thickness of 0.1 to 10 micrometers is applied to a clean substrate surface either through spray coating, brush coating or dip coating. Multiple layers ranging in thickness from about 0.1 to 10 micrometers can also be applied to the substrate surface. After the solvent mixture is applied to the substrate surface, it is allowed to dry before the biomimetic surfactant coating is applied.

In a third preferred tie layer method, a silicone polycarbonate co-polymer is applied to the substrate surface. Preferably, about 0.1 to about 10 weight percent silicone polycarbonate co-polymer is dissolved in tetrahydrofuran (THF) solvent. Alternatively, dimethylacetamide, hexane or toluene can be used to dissolve the silicone polycarbonate material. Preferably, a coating solution with a range of about 0.1 to about 10 weight percent of silicone polycarbonate co-polymer in hexane is prepared.

In the third embodiment, a layer of about 100 nanometers thick is applied to a clean, bare substrate surface. Multiple layers ranging in thickness from about 1 to about 10 micrometers can also be applied. After the solvent mixture is applied to the substrate surface, it is dried in ambient air before the biomimetic surfactant coating is applied.

In a fourth preferred tie layer method, a polyurethane polycarbonate co-polymer, such as the "Bionate" family of polyurethane polycarbonate polymers manufactured by DSM-PTG, is applied to the substrate surface. The polyurethane polycarbonate copolymer is dissolved in tetrahydrofuran (THF) in a range of about 0.1 to about 10 weight percent polyurethane polycarbonate co-polymer. Alternatively, dimethyacetamide (DMAC) can be used to dissolve the polyurethane polycarbonate co-polymer material.

In the fourth embodiment, a layer about 100 nanometers thick is applied to a clean substrate surface. Multiple layers ranging in thickness from about 1 to about 10 micrometers can also be applied. After the solvent mixture is applied to the substrate surface, it is allowed to dry in ambient air before the biomimetic surfactant coating is applied.

In addition to the solution processes just described, a hydrophobic tie layer can also be applied to a substrate using any one of the following alternate methods including powder coating, melt extrusion, Langmuir-Blodgett process, gas plasma deposition, chemical vapor deposition, physical deposition process, spray coating, dip coating, or spin coating.

Although it is preferred that the hydrophobic constituent be dissolved in tetrahydrofuran THF to create a hydrophobic tie layer solution, it is contemplated that other solvents including ethanol, methanol, ethylacetate, dimethylformamide (DMF), dimethyacetamide (DMAC), dimethylsulfoxide (DMSO), dioxane, N-methylpyrollidone, chloroform, hexane, heptanes, cyclohexane, toluene, formic acid, acetic acid, and/or dichloromethane could be used to dissolve the hydrophobic constituent to create the tie layer solution.

Single or multiple coats of the tie layer solution may be applied to the substrate surface to achieve the desired thickness. Substrate materials including biocompatible metals and polymers including, but not limited to, polyurethane, silicone, polyethylene, polypropylene, polyether block amide, polyester, polyether ether ketone, titanium, titanium alloys, stainless steel, gold, platinum, palladium, and MP35N may also be used.

Alternatively, the surface of the substrate can be modified through the addition of a hydrophobic dopant. The dopant can be in the form of a small amount of a hydrophobic component that is added during processing of the substrate material. After the polymeric material including the dopant is extruded to its final form, it is ready to be coated with the biomimetic surfactant polymer. Erucamide is one preferred dopant.

In a first dopant embodiment, about 1 weight percent erucamide is first dissolved into tetrahydrofuran (THE), toluene or other compatible organic solvent. This solvent mixture is then combined into the substrate polymer prior to extrusion. Although about 1 weight percent erucamide is preferred, a range from about 0.1 to 10 weight percent erucamide can be dissolved into the organic solvent to create the dopant mixture.

About 1, to 30 weight percent of the dopant mixture is then incorporated into the substrate polymer. The solvent mixture is incorporated into the substrate polymer and dried before it is extruded into the final form. Substrate polymers capable of being doped include biocompatible polymers including, but not limited to, polyurethane, polyester, and polyether ether ketone, preferably polyurethane and polycarbonate.

After the substrate surface has been modified, either through the addition of a hydrophobic tie layer or hydrophobic dopant, the biomimetic coating such as poly(N-vinyldextran aldonamide-co-N-vinylhexanamide) is applied to the modified substrate surface. However, before applying the biomimetic coating to the modified surface, the hydrophobicity of the substrate surface is characterized to ensure proper surfactant coating adhesion. The Sessile drop method, which measures the contact angle of a droplet of liquid to a substrate surface, is preferred for determining the hydrophobic quality of the substrate surface to ensure adequate surfactant adhesion.

Figure 3:
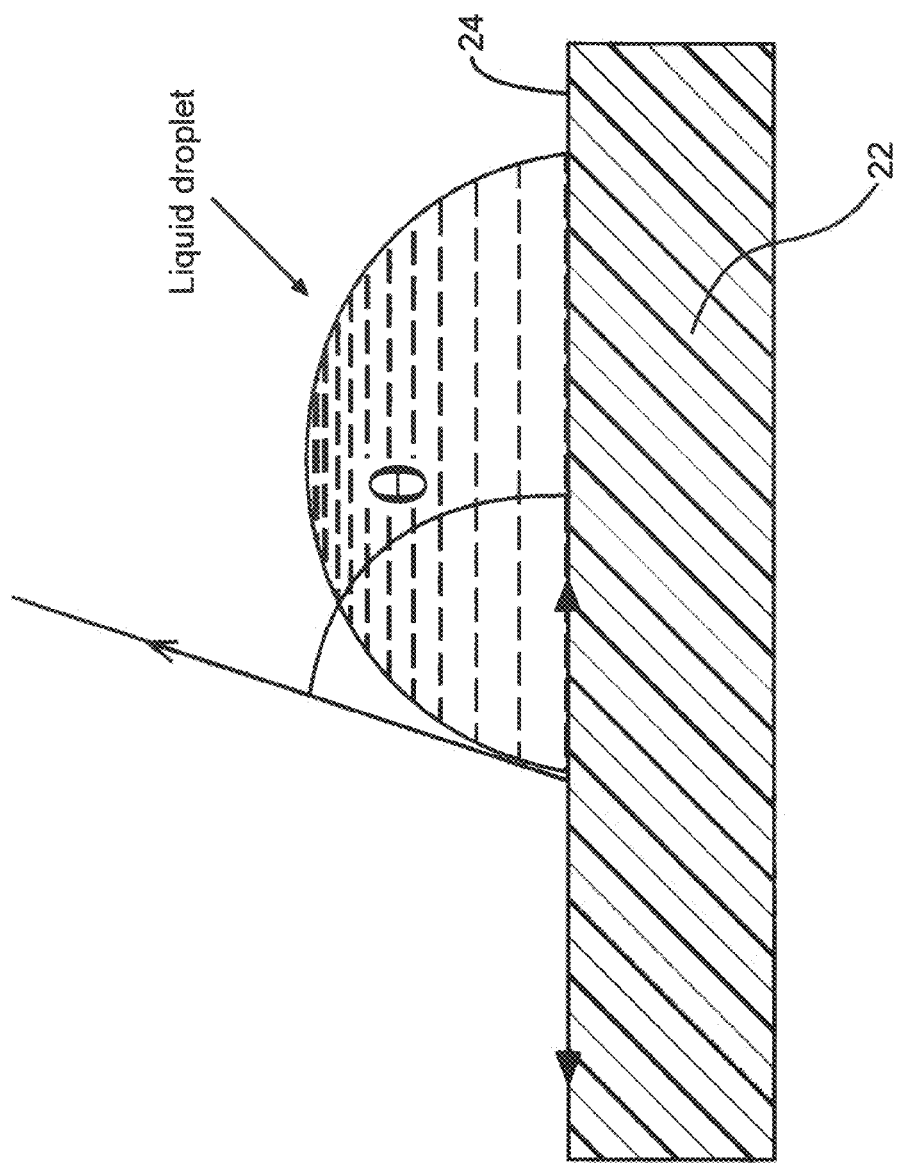
FIG. 3 is a cross sectional view showing how the contact angle is measured.

In the Sessile drop method, a droplet of liquid is placed on the substrate surface and the contact angle is measured. The contact angle is defined as the angle at which the liquid to air interface meets the solid substrate surface as shown in FIG. 3.

To characterize the hydrophobicity of the modified substrate surface, a droplet of water is placed on the modified substrate surface and the contact angle is measured using the Sessile drop method. A satisfactorily hydrophobic surface has a contact angle greater than 40 degrees.

Once the substrate surface is adequately modified, a solution of the biomimetic coating is prepared. In a preferred embodiment, an aqueous solution with a range from about 1 to about 25 weight percent poly(N-vinyldextran aldonamide-co-N-vinylhexanamide) is prepared. Alternatively, the aqueous surfactant solution can be blended with isopropyl alcohol. When using isopropyl alcohol, a solvent solution of about 45 to about 55 weight percent isopropyl alcohol is added to the aqueous surfactant solution.

Once the mixture of surfactant and solvent is created, it is applied to the substrate surface and allowed to dry in ambient air. It is preferred that the surfactant solution be applied through dip coating. The hydrophobicly modified substrate surface binds with the hydrophobic side chains of the non-thrombogenic coating material to ensure proper adhesion.

It is contemplated that other means such as spray coating, spin coating, or brush application could also be used to apply the biomimetic coating to the modified substrate surface.

Thus, the present invention teaches various formulations and methods of incorporation of the biomimetic surfactant into the substrate of a medical device. The thusly modified polymeric substrate has improved infacial blood compatibility including the ability to prevent the formation of blood clots. This makes the polymeric material a desirable candidate for use in the manufacture of implantable medical devices.

What is claimed is:

1. A substrate, which comprises:
   a) a substrate composed of a material selected from the group consisting of silicone, polyether block amide (PEBA), polycarbonate and polyurethane, wherein the substrate has a surface;
   b) a hydrophobic tie layer having opposed top and bottom tie layer surfaces and a surface contact angle greater than about 40°, wherein the hydrophobic tie layer consists of a solvent and an unsaturated carboxylic acid amide at a concentration from about 0.1 to about 10 weight percent within the solvent; and
   c) a biomimetic surfactant comprising an alkyl chain, wherein the hydrophobic tie layer is positioned between the substrate surface and the biomimetic surfactant; and
   d) wherein the unsaturated carboxylic acid amide within the hydrophobic tie layer hydrophobically bonds to the alkyl chain of the biomimetic surfactant along the tie layer top surface and the unsaturated carboxylic acid amide hydrophobically bonds to the substrate surface along the tie layer bottom surface.

2. The substrate of claim 1 wherein the hydrophobic tie layer comprises erucamide.

3. The substrate of claim 1 wherein the biomimetic surfactant is selected from the group consisting of poly(N-vinyl-dextran aldonamide-co-N-vinylhexanamide), poly(N-vinyl dextran aldonamide-co-N-vinyl dodecanoamide)(PNVDA-co-PNVL), poly (N-vinyl hexyl amine-co-N-vinyl heparinamine)(PNVHA-co-PNVHep A), poly(N-vinyl hexyl amine-co-N-vinyl heparinamine-co-N-vinyl maltonoamide) (PNVHA-co-PN-VHepA-co-PNVM), and poly (N-vinyl-5-peptidyl-pentylamine-co-N-vinyl-dextranaldonamine-co-N-vinyl hexyl amine (PVAm(Pep:Dex:Hex)).

4. The substrate of claim 1 wherein the substrate surface is a surface selected from the group of medical devices consisting of a pacemaker, a defibrillator, a neurostimulator, an introducer, a lead, a catheter, and a stent.

5. The substrate of claim 1 wherein a thickness of the hydrophobic tie layer is from about 0.1 nanometers to about 2.5 nanometers.

6. The substrate of claim 1 wherein a thickness of the hydrophobic tie layer is from about 2.5 nanometers to about 1 micrometer.

7. The substrate of claim 1 wherein a thickness of the hydrophobic tie layer is from about 1 micrometer to about 100 micrometers.

8. The substrate of claim 1 wherein the solvent is selected from the group consisting of tetrahydrofuran, dimethylsulfoxide, ethanol, methanol, ethylacetate, dimethylformamide, dimethylacetamide, dioxane, N-methyl pyrollidone, chloroform, hexane, heptanes, cyclohexane, toluene, formic acid, acetic acid, dichloromethane, and mixtures thereof.

9. A method for increasing the hydrophobicity of a substrate surface to enhance the adhesion of a biomimetic surfactant polymer to the substrate surface, the method comprising the steps of:
   a) providing a substrate composed of a material selected from the group consisting of silicone, polyurethane, polyether block amide (PEBA), and polycarbonate, wherein the substrate has a substrate surface;
   b) providing a biomimetic surfactant polymer comprising an alkyl chain;
   c) providing a hydrophobic tie layer having opposed top and bottom hydrophobic tie layer surfaces, wherein the hydrophobic tie layer consisting of a solvent and an unsaturated carboxylic acid amide at a concentration ranging from about 0.1 to about 10 weight percent within the solvent;
   d) applying the bottom hydrophobic tie layer surface to the substrate surface to thereby create a surface contact angle greater than about 40°;
   e) applying the biomimetic surfactant to the top polymer hydrophobic tie layer surface; and
   f) wherein the unsaturated carboxylic acid amide within the hydrophobic tie layer hydrophobically bonds to the substrate surface along the bottom hydrophobic tie layer surface and the unsaturated carboxylic acid amide within the hydrophobic tie layer hydrophobically bonds to the alkyl chain of the biomimetic surfactant polymer along the top hydrophobic tie layer surface.

10. The method of claim 9 wherein the unsaturated carboxylic acid amide comprises erucamide.

11. The method of claim 9 wherein the solvent is selected from the group consisting of tetrahydrofuran, dimethylsulfoxide, ethanol, methanol, ethylacetate, dimethylformamide, dimethylacetamide, dioxane, N-methyl pyrollidone, chloroform, hexane, heptanes, cyclohexane, toluene, formic acid, acetic acid, dichloromethane, and mixtures thereof.

12. The method of claim 9 wherein the substrate surface is a surface selected from the group of medical devices consisting of a pacemaker, a defibrillator, a neurostimulator, an introducer, a lead, a catheter, and a stent.

13. The method of claim 9 wherein the biomimetic surfactant polymer is selected from the group consisting of poly(N-vinyl dextran aldonamide-co-N-vinyl hexanoamide), poly (N-vinyl dectran aldonamide)(PNVDA-co-PNVH), poly(N-vinyl dextran aldonamide-co-N-vinyl dodecanoamide)(PNVDA-co-PNVL), poly (N-vinyl hexyl amine-co-N-vinyl heparinamine)(PNVHA-co-PNVHep A), poly(N-vinyl hexyl amine-co-N-vinyl heparinamine-co-N-vinyl maltonoamide) (PNVHA-co-PN-VHepA-co-PNVM), and poly (N-vinyl-5-peptidyl-pentylamine-co-N-vinyl-dextranaldonamine-co-N-vinyl hexyl amine (PVAm(Pep:Dex:Hex)).

14. A substrate, which comprises:
   a) a substrate composed of a material selected from the group consisting of silicone, polyether block amide (PEBA), polycarbonate and polyurethane, wherein the substrate has a surface;
   b) a hydrophobic tie layer having opposed top and bottom tie layer surfaces and a contact angle greater than 40°, wherein the tie layer consists of a tetrahydrofuran solvent and erucamide at a concentration ranging from about 0.1 to about 10 weight percent the solvent;
   c) a biomimetic surfactant of poly(N-vinyl dextran aldonamide-co-N-vinyl hexanamide) comprising an alkyl chain, wherein the hydrophobic tie layer is positioned between the substrate surface and the biomimetic surfactant; and
   d) wherein the erucamide within the hydrophobic tie layer hydrophobically bonds with the substrate surface along the bottom tie layer surface; and
   e) wherein the erucamide within the hydrophobic tie layer hydrophobically bonds with the alkyl chain within the biomimetic surfactant along the top tie layer surface, thereby creating a hydrophobic bond therebetween the substrate surface and the biomimetic surfactant.

15. The substrate of claim 14 wherein the substrate surface is a surface selected from the group of medical devices comprising of a pacemaker, a defibrillator, a neurostimulator, an introducer, a lead, a catheter, and a stent.

* * * * *